United States Patent
Shearn

(10) Patent No.: US 7,338,472 B2
(45) Date of Patent: Mar. 4, 2008

(54) DIRECTLY ENGAGED SYRINGE DRIVER SYSTEM

(75) Inventor: James G. J. Shearn, Basingstoke (GB)

(73) Assignee: Cardinal Health 303, Inc., San Diego, CA (US)

( * ) Notice: Subject to any disclaimer, the term of this patent is extended or adjusted under 35 U.S.C. 154(b) by 402 days.

(21) Appl. No.: 10/657,930

(22) Filed: Sep. 9, 2003

(65) Prior Publication Data

US 2004/0049161 A1    Mar. 11, 2004

Related U.S. Application Data

(62) Division of application No. 09/247,756, filed on Feb. 9, 1999, now Pat. No. 6,645,177.

(51) Int. Cl.
*A61M 37/00* (2006.01)
(52) U.S. Cl. .................................... 604/155
(58) Field of Classification Search ............ 604/65, 604/66, 67, 131, 132, 134, 135, 152, 154, 604/155, 156, 208, 211
See application file for complete search history.

(56) References Cited

U.S. PATENT DOCUMENTS

| | | | |
|---|---|---|---|
| 3,623,474 A * | 11/1971 | Heilman et al. ............ 600/432 |
| 3,812,843 A * | 5/1974 | Wootten et al. ............ 600/432 |
| 3,880,138 A | 4/1975 | Wootten et al. |
| 4,196,730 A * | 4/1980 | Wilson ....................... 604/155 |
| 4,424,720 A * | 1/1984 | Bucchianeri ............ 74/424.78 |
| 4,508,532 A | 4/1985 | Drews et al. |
| 4,648,872 A | 3/1987 | Kamen |
| 4,767,406 A | 8/1988 | Wadham et al. |
| 4,978,335 A | 12/1990 | Arthur, III |
| 5,219,099 A * | 6/1993 | Spence et al. ............. 222/325 |
| 5,236,416 A | 8/1993 | McDaniel et al. |
| 5,545,140 A | 8/1996 | Conero et al. |
| 5,647,853 A * | 7/1997 | Feldmann et al. .......... 604/155 |
| 5,925,018 A * | 7/1999 | Ungerstedt .................. 604/155 |

(Continued)

FOREIGN PATENT DOCUMENTS

AU    199745341 A1    5/1998

(Continued)

OTHER PUBLICATIONS

International Search Report - International Application No. PCT/US00/03270; International Filing Date: Feb. 8, 2000.

*Primary Examiner*—Manuel Mendez
(74) *Attorney, Agent, or Firm*—McDermott Will & Emery

(57) ABSTRACT

A syringe driver system comprises a rotatable threaded lead screw shaft and a plunger which directly engages the threaded shaft such that rotation of the shaft drives the plunger into the syringe body. The plunger is formed with a threaded shaft engaging portion in the form of a half nut to engage with and follow the threaded shaft. The syringe driver system further comprises a guide system to secure the plunger in direct engagement with the threaded shaft and to prevent rotation of the plunger. An arm of the plunger stem carries markers useful in determining the near end of infusion. The syringe body carries a marker or markers useful in determining a characteristic about the syringe, such as its volume.

25 Claims, 6 Drawing Sheets

| U.S. PATENT DOCUMENTS | | | |
|---|---|---|---|
| 5,954,697 A | 9/1999 | Srisathapat et al. | |
| 6,423,035 B1 * | 7/2002 | Das et al. | 604/155 |
| 6,485,465 B2 * | 11/2002 | Moberg et al. | 604/154 |

FOREIGN PATENT DOCUMENTS

| EP | 0 566 825 A1 | 10/1993 |
|---|---|---|
| EP | 0 654 279 A2 | 5/1995 |
| WO | WO89/11310 | 11/1989 |
| WO | WO 89/11310 | 11/1989 |
| WO | WO99/27981 | 6/1999 |
| WO | WO 99/27981 | 6/1999 |

* cited by examiner

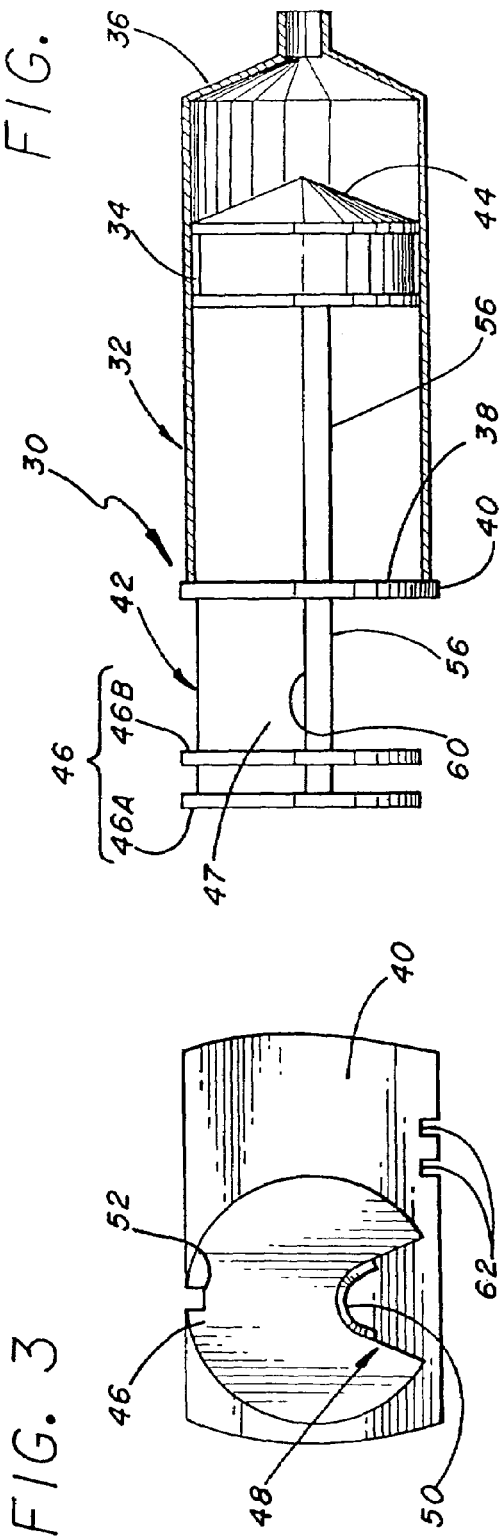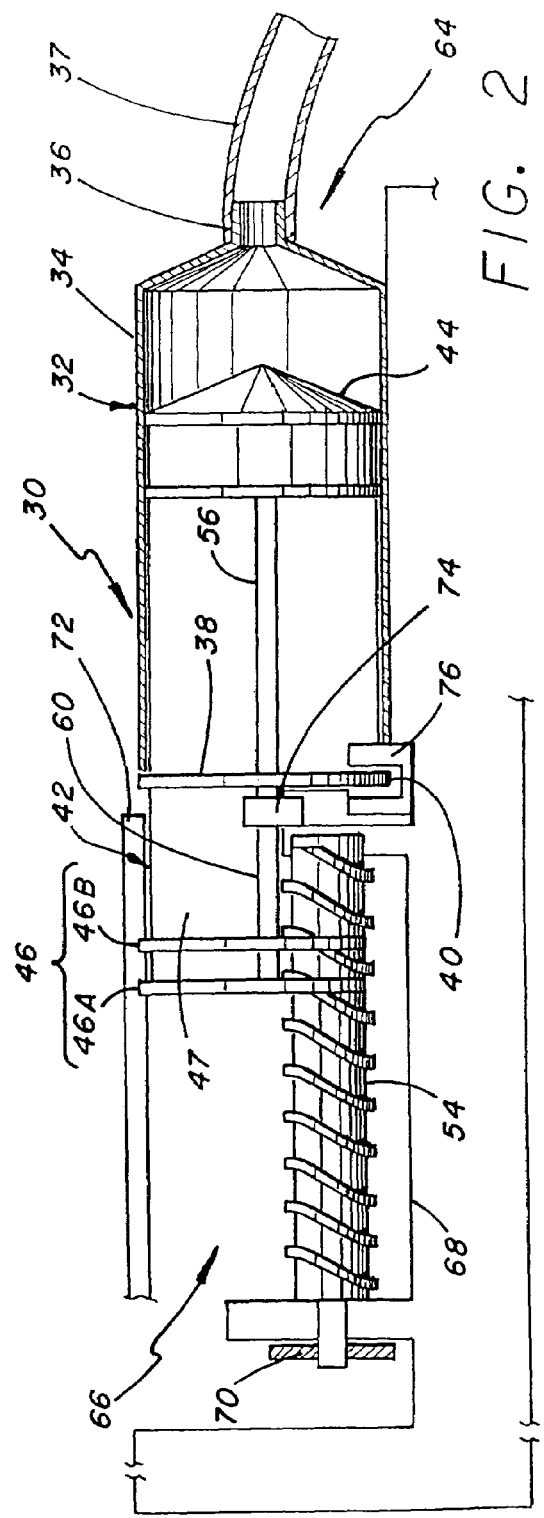

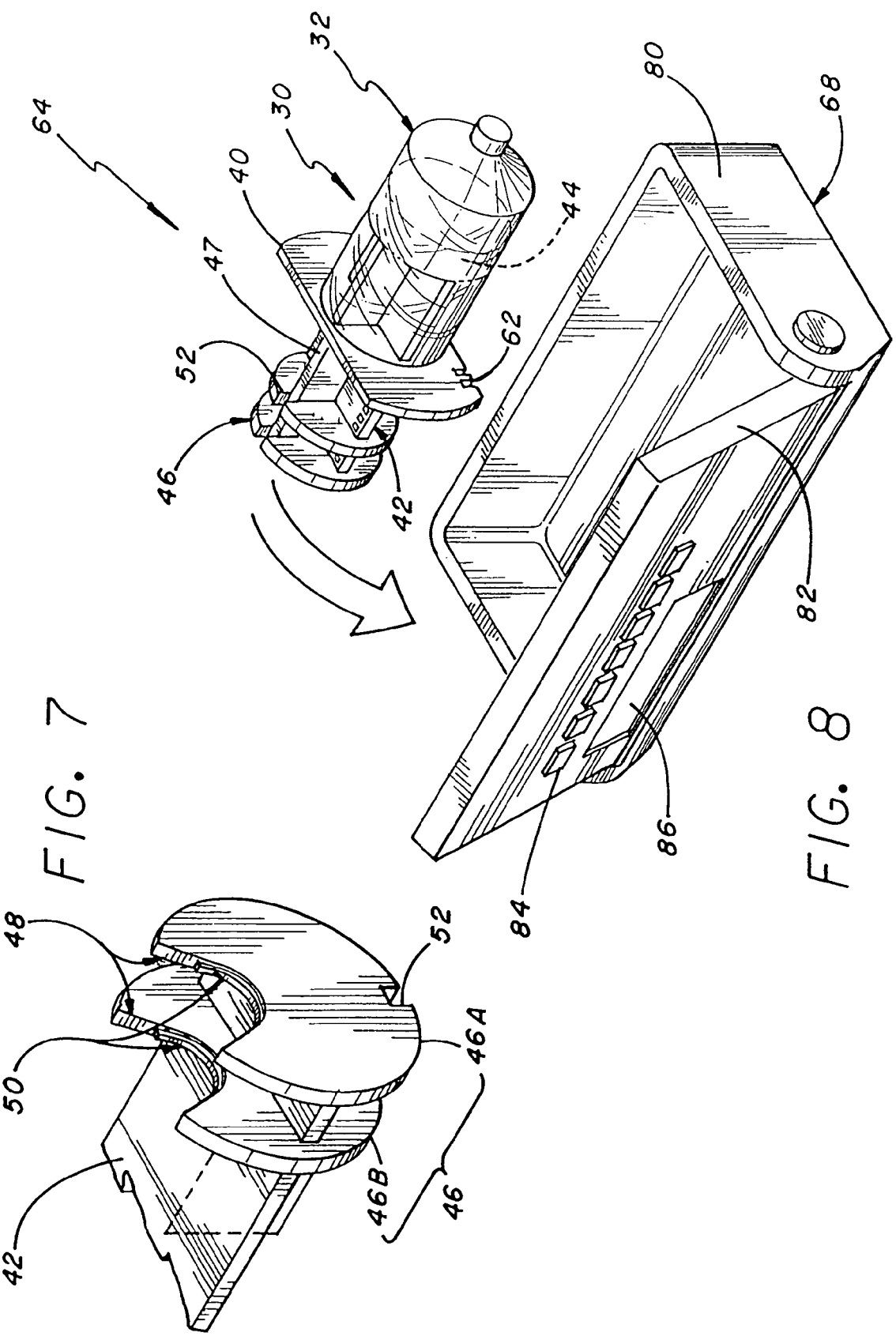

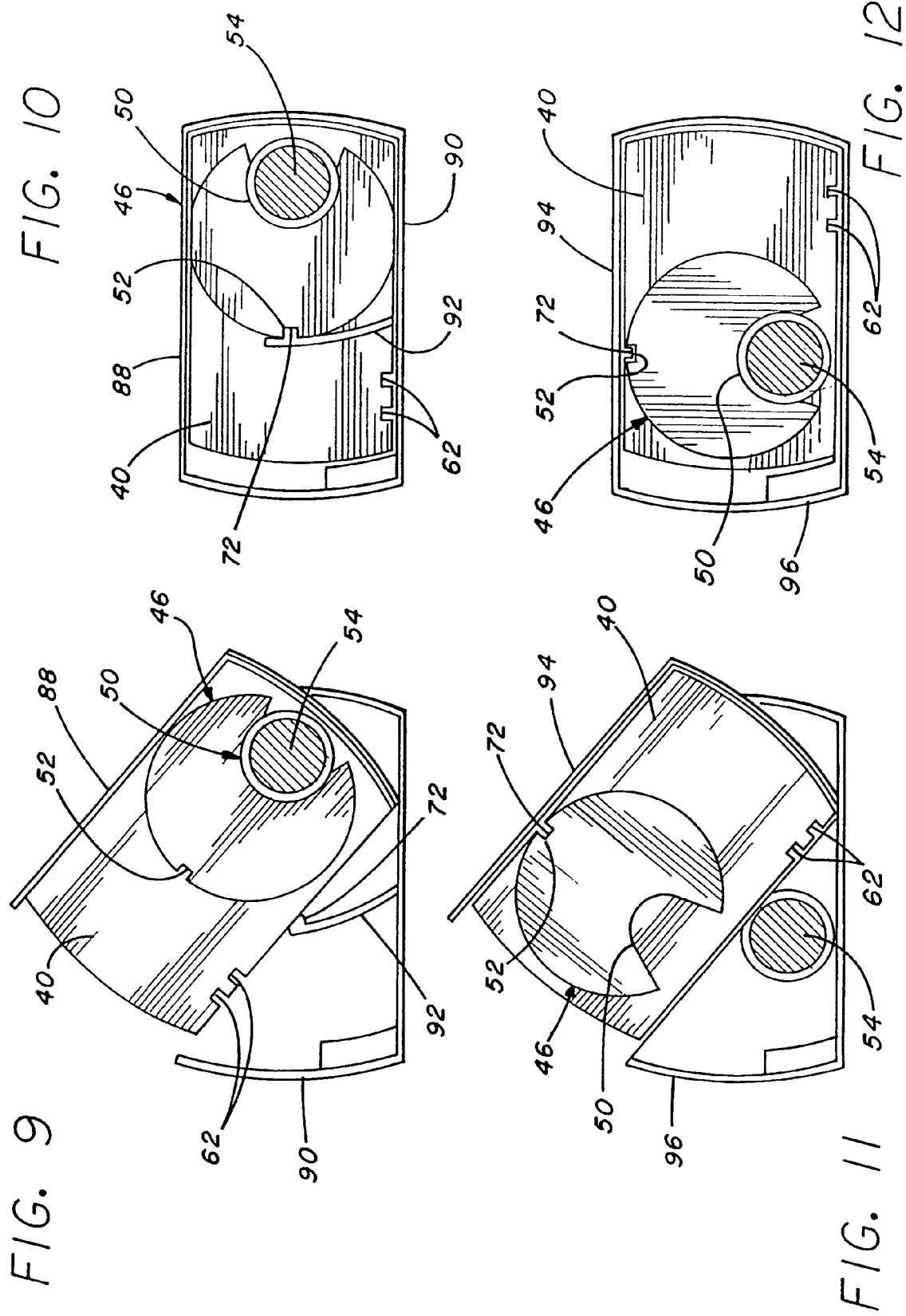

DIRECTLY ENGAGED SYRINGE DRIVER SYSTEM

This is a division of application Ser. No. 09/247,756, filed Feb. 9, 1999 now U.S. Pat. No. 6,645,177.

BACKGROUND OF THE INVENTION

The invention relates generally to drug infusion systems and, more particularly, to a syringe driver for expelling fluid from a syringe and a syringe for use in the syringe driver.

Syringe drivers are used in the medical environment to infuse a given dose of a medicament into a patient from a syringe engaged with the driver. The medicament is generally infused at a regular rate over a period of time which may vary from, for example, an hour to a number of days. Referring to FIG. 1, a conventional ambulatory syringe driver 10 comprises a housing 12 which includes a rotatable threaded shaft or lead screw 14 driven by a motor located within the housing. The motor is powered by batteries also located in the housing. The threaded shaft 14 is exposed and a driver block 16 with a threaded bore is mounted on the threaded shaft such that rotation of the shaft drives the driver block along the shaft. The driver block is provided with a de-clutch button 18 which, when depressed, de-clutches the driver block from the threaded shaft to allow free movement of the driver block along the shaft. The driver block has a clip or slot 20 by which a plunger 22 of a syringe 24 can be secured to the driver block for controlled movement of the plunger 22.

While FIG. 1 represents a typical current ambulatory syringe driver system, some non-ambulatory systems have differences. In such non-ambulatory syringe driver systems, the lead screw and driver block are enclosed within the casework of the device, usually running parallel to, but spaced apart from the syringe barrel. An arm or slide extends sideways from the driver block out through the casework, to engage the syringe plunger. The arm terminates with a plunger holder, which usually incorporates a mechanism for remotely de-clutching the half nut within the driver block. Thus, a driving force can be applied to the syringe without exposing the lead screw. Additionally, many such non-ambulatory systems are powered by both main power (wall power) and battery power.

In the operation of the syringe driver shown in FIG. 1, a syringe having a cylindrical syringe body and a plunger slidably mounted in the body is clamped 26 to the housing by its body. The free end of the plunger extends from the syringe body and lies parallel with, but spaced apart from, the threaded shaft. The de-clutch button 18 is depressed to allow free movement of the driver block along the threaded shaft such that the slot in the driver block is aligned with and receives the free end of the plunger. Once the free end of the plunger has been secured to the driver block, the de-clutch button is released and the driver block once again engages the threaded shaft. When the motor of the driver is actuated, the driver block is driven towards the syringe body thereby driving the plunger into the syringe body causing fluid in the syringe body to be expelled and infused into the patient.

A disadvantage of such a syringe driver, as described above and shown in FIG. 1, is that the overall size of the syringe driver with respect to the syringe is large. This is due at least in part to the driver block that is mounted on the threaded shaft. In particular, the driver block 16 accounts for a significant portion of the overall size of the syringe driver 10 in that it spaces the syringe plunger 22 away from the threaded shaft 14 and requires an additional length to the threaded shaft to accommodate the driver block when the largest syringe specified for the driver 10 is used and the driver block must be moved to the far end of its travel to receive the plunger of that syringe. This is necessary because of the internal components of the driver block, such as the de-clutch button 18, the internal threaded portion, and the slot 20 of the driver block. The threaded portion must be long enough to firmly engage the threaded shaft and must have means to hold the threads in contact with the threaded shaft even under heavy loads provided by the syringe or downstream infusion system. However, certain applications, such as ambulatory uses, would benefit from a smaller size syringe driver system.

Another disadvantage associated with conventional syringe drivers is that there is a certain amount of play between the driver block 16 and the threaded shaft 14 which gives rise to hysteresis in the movement of the block with respect to the threaded shaft as well as some backlash. It should be noted that the driver block, as well as the housing, motor, threaded shaft, and syringe clamp are all reusable elements. Because the driver block is a reusable element, such hysteresis and backlash tend to worsen over time because of wear on the driver block. It would also be of value to lessen the possibility of wear of the driver block.

Additionally, driver blocks, depending on their complexity, can themselves add a significant expense to the syringe driver system. Further, should replacement due to wear be required, the labor needed to disassemble the syringe driver housing, as well as the "down time" of the syringe driver system to replace the driver block are undesirable costs for a hospital or other health care institution. Thus, an improvement over existing driver block designs would be desirable, as well as making syringe driver systems smaller to make them more useful in an ambulatory application.

Many ambulatory syringe drivers presently available are calibrated in millimeters per hour; i.e., a distance rate, as they lack the complexity to determine the size of syringe fitted. Most medical infusion prescriptions are written in volume to be infused; i.e., milliliters per hour. Having to convert milliliters per hour to millimeters per hour can impose an additional undesired step on medical care providers. However, most non-ambulatory syringe drivers are calibrated in milliliters per hour as they tend to be fitted with systems that can identify the syringe type by its external diameter. It would be of benefit to provide an ambulatory syringe driver system that can automatically recognize the syringe installed and can therefore accept a flow instruction in volume per time format, such as milliliters per hour to make setting the rate of infusion easier.

Additionally, it is also convenient for a pump or driver to present the care provider with a warning that the syringe is nearly exhausted. This has been found to be beneficial when the preparation of a patient's medicants takes some time but cannot be prepared too far ahead of time. With a near-end-of-infusion warning, preparation of those medicants can begin. As mentioned above, ambulatory syringe drivers typically lack complexity and in most cases, do not include a mechanism to determine the near end of infusion point. They usually only provide an alarm at the end of infusion when the syringe is exhausted. Some non-ambulatory devices however have mechanisms to determine not only the existence of linear movement of the syringe plunger but also the near-end-of-infusion point and these features would be desirable in ambulatory designs as well.

Hence, those skilled in the art have recognized a need for a syringe driver system having a reduced size as well as one with fewer moving parts subject to wear and replacement.

Additionally, an ambulatory syringe driver system light and small enough to be carried by a person and capable of receiving infusion instructions in volume per unit time as well as one that detects linear movement of the syringe plunger and provides a near end of infusion warning have been recognized as needed. It has also been recognized by those skilled in the art that it would be of value to have a syringe driver system that is lower in cost and easier to manufacture. The present invention satisfies these needs as well as others.

SUMMARY OF THE INVENTION

Briefly, and in general terms, in one aspect the invention is directed to a syringe driver system having a plunger and a threaded shaft for driving fluid from a syringe body mounted on the syringe driver in a manner that provides a greater degree of infusion accuracy.

In another aspect, a rotatable threaded shaft is directly engaged by a plunger such that rotation of the shaft drives the plunger into the syringe body and expels the syringe contents. In detailed aspects, the plunger is formed with a shaft engaging portion to engage with and follow the threaded shaft. The shaft engaging portion comprises a threaded portion molded into the plunger, and the shaft engaging portion comprises at least one recessed half-nut. In another detailed aspect the plunger comprises a flange having at least one disk, the shaft engaging portion is part of the flange, and the edges of the flange adjacent the shaft engaging portion are formed to guide the shaft engaging portion onto the threaded shaft.

In further detailed aspects the syringe driver system further comprises a guide system to secure the plunger in direct engagement with the threaded shaft and to prevent rotation of the plunger. In yet another detailed aspect, the guide system comprises a first guiding element running substantially parallel to the threaded shaft and a second guiding element carried by the plunger at a position substantially opposite the position at which the plunger engages the threaded shaft such that the first and second guiding elements engage.

In another aspect, the system for infusing fluid comprises a cover and a base for accommodating the threaded shaft, syringe, and motor. In a detailed aspect, the apparatus further comprises a control system for monitoring operating parameters of the apparatus and controlling the rotation of the motor and a detection system for detecting movement of the plunger. In another detailed aspect, the syringe includes one or more identification markings indicative of a characteristic of the syringe, such as its volume, the detection system includes a detector for detecting the identification markings and the detector system provides a signal to the control system in accordance with the identification markings detected. In a further detailed aspect, the stem of the plunger has an elongate arm provided with a plurality of markings to define a linear grid to indicate the movement and position of the plunger within the syringe body, the detection system includes a plurality of detectors for detecting the markings and the detector system provides signals to the control system in accordance with the markings detected.

In yet another detailed aspect, the detection system includes a light source, the detection system positioned adjacent the markings of the plunger stem arm such that the light source is on one side of the arm and the plurality of detectors is on the opposite side of the arm and wherein the markings on the arm at a near end of infusion (NEOI) point of the syringe have a first size and the markings elsewhere on the arm have a second size different than the first size such that the markings at the NEOI point allow illumination of a first number of the detectors and the markings elsewhere allow illumination of a second number of detectors different than the first number of detectors.

In yet a further aspect, a plunger for engaging a threaded shaft and for expelling fluid from a syringe body comprises a stem, a stopper positioned at an end of the stem, the stopper sized to fit within the syringe body and a flange positioned at the end of the stem opposite the stopper, the flange having a threaded portion sized to engage the threaded shaft.

In yet another aspect, a syringe for use in a fluid delivery apparatus having a threaded shaft comprises a syringe body, a stem, a stopper positioned at an end of the stem, the stopper sized to fit within the syringe body, and a flange positioned at the end of the stem opposite the stopper and outside of the syringe body, the flange having a threaded portion sized to engage the threaded shaft.

These and other aspects and advantages of the invention will become apparent from the following detailed description and the accompanying drawings, which illustrate by way of example the features of the invention.

BRIEF DESCRIPTION OF THE DRAWINGS

FIG. 2 is a side view of a syringe in accordance with aspects of the invention shown in partial cross section and connected to an infusion administration set, the syringe engaged with a part of a syringe driver embodying further aspects, other parts of the syringe driver not being shown;

FIG. 3 is an end view of the syringe shown in FIG. 2 showing a guide rail slot in the plunger, the half nut, and identification markers in the body flange;

FIG. 4 is a partial cross-section of the syringe shown in FIG. 2 more clearly showing that there exists no bottom arm of the syringe plunger stem so that the plunger and lead screw of the syringe driver may be positioned more closely together;

FIG. 7 is a perspective view of a half nut formed in the plunger flanges of the syringe shown in FIGS. 2 through 4 and which may also be formed in the syringe of FIGS. 5 and 6;

FIG. 8 is an example of an ambulatory syringe driver system usable with the syringes shown in previous figures, and indicating the placement of the syringe of FIGS. 2 through 4 to be inserted in the syringe driver, the casing for the syringe driver being in an open condition;

FIGS. 9 and 10 demonstrate a mounting arrangement of a syringe in accordance with aspects of the invention where the guide device comprises an arm that engages the slots of the syringe plunger flanges. In particular, FIG. 9 shows a syringe partially inserted into a syringe driver and engaged with the lead screw, the casing of the driver being in an open condition, and FIG. 10 shows the syringe fully inserted and ready for use;

FIGS. 11 and 12 show an alternate arrangement for mounting a syringe in accordance with aspects of the invention wherein the lead screw is located at the bottom of the casing and the guide rail is at the top. FIG. 11 shows the syringe driver casing in an open position while FIG. 12 shows the casing in a closed condition with the syringe secured in position for the infusion of its contents to a patient by operation of the syringe driver.

DETAILED DESCRIPTION OF PREFERRED EMBODIMENTS

Figure 1:
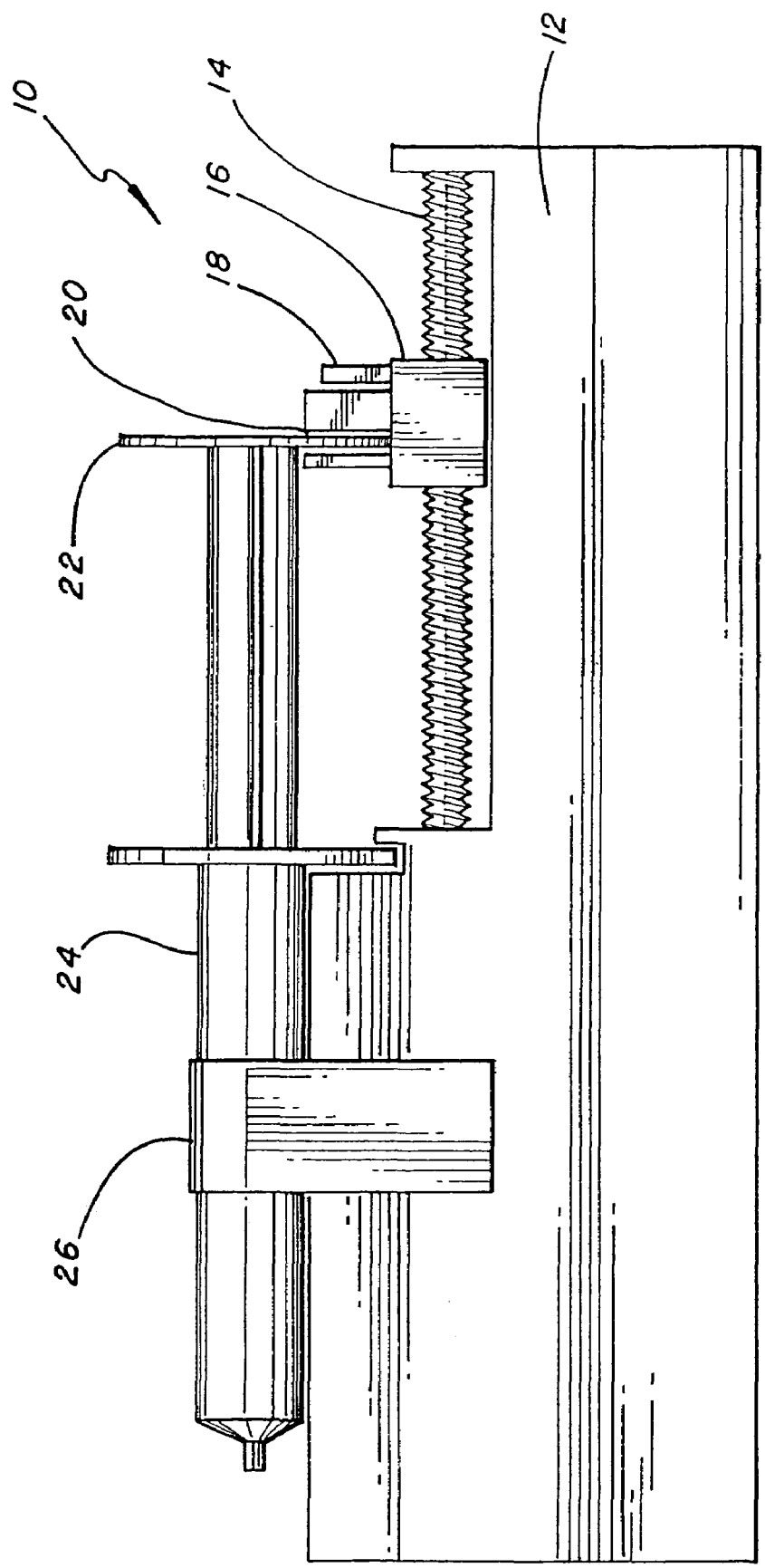
FIG. 1 is a schematic side view of a conventional, prior art ambulatory syringe driver system with a mounted syringe showing a drive block connected between the lead screw of the syringe driver and the syringe plunger for translating the rotational motion of the lead screw to linear motion of the plunger for expelling the contents of the syringe.

Turning now to the drawings, in which like reference numerals are used to designate like or corresponding elements among the several figures, in FIG. 2 in a generally schematic view there is shown a syringe 30 for use with a syringe driver 66 embodying aspects of the present invention and together forming a syringe driver system 64. The syringe 30 includes a syringe body 32 having a side wall 34 which in two embodiments may be cylindrical or elliptical in shape, formed with a nozzle end 36 at its distal tip and an open end 38 at its proximal end terminating in an outwardly directed body flange 40. At the nozzle end 36, a fluid administration set 37 may be mounted. Such sets are well known to those skilled in the art and include tubing, and in some cases, valves, injector ports, and clamps. Other devices may also be included in the administration set.

In one embodiment, as shown in FIG. 3, the syringe body flange 40 is substantially rectangular and the syringe body 32 is positioned to one side of the syringe body flange 40 so that one side of the flange 40 projects farther from the syringe body 32 than at the other side. In other embodiments the shape of the syringe body flange 40 may deviate from the substantially rectangular shape shown in FIG. 3.

FIG. 4 presents a view of the syringe 30 without the driver 66 of FIG. 1. A plunger 42, as shown in FIGS. 2, 4, and 8 is slidably inserted in the syringe body 32 and has a rubber-or latex-free stopper 44 fitted at one end within the syringe body and a plunger flange 46 at its free end. The plunger flange 46 in this embodiment comprises two co-axial and parallel spaced-apart disks 46A and 46B. In contrast to conventional syringe plungers which have a cruciform stem, the stem 47 of the plunger 42 shown in FIGS. 2, 4, and 8 only has three stem arms, the lowermost stem arm being omitted so that the lead screw 54 can be accommodated as shown in FIG. 2.

Figure 5:
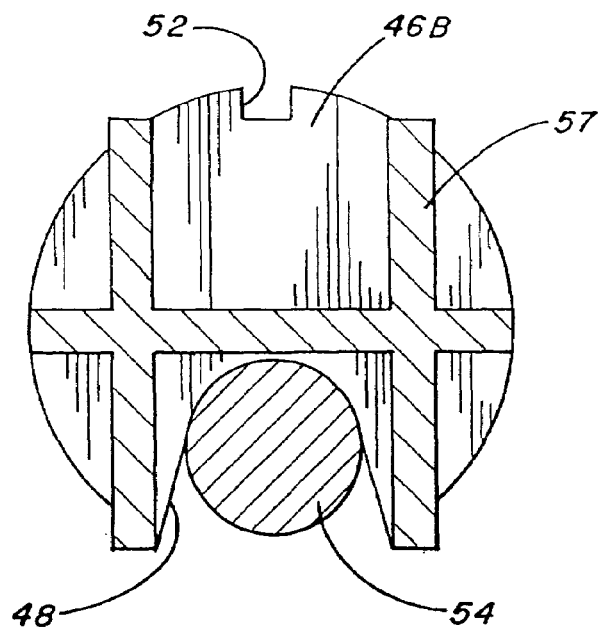
FIG. 5 is a cross-section view of an alternate embodiment of a syringe plunger showing an H-section configuration of the stem and the position of the lead screw in the stem.
Figure 6:
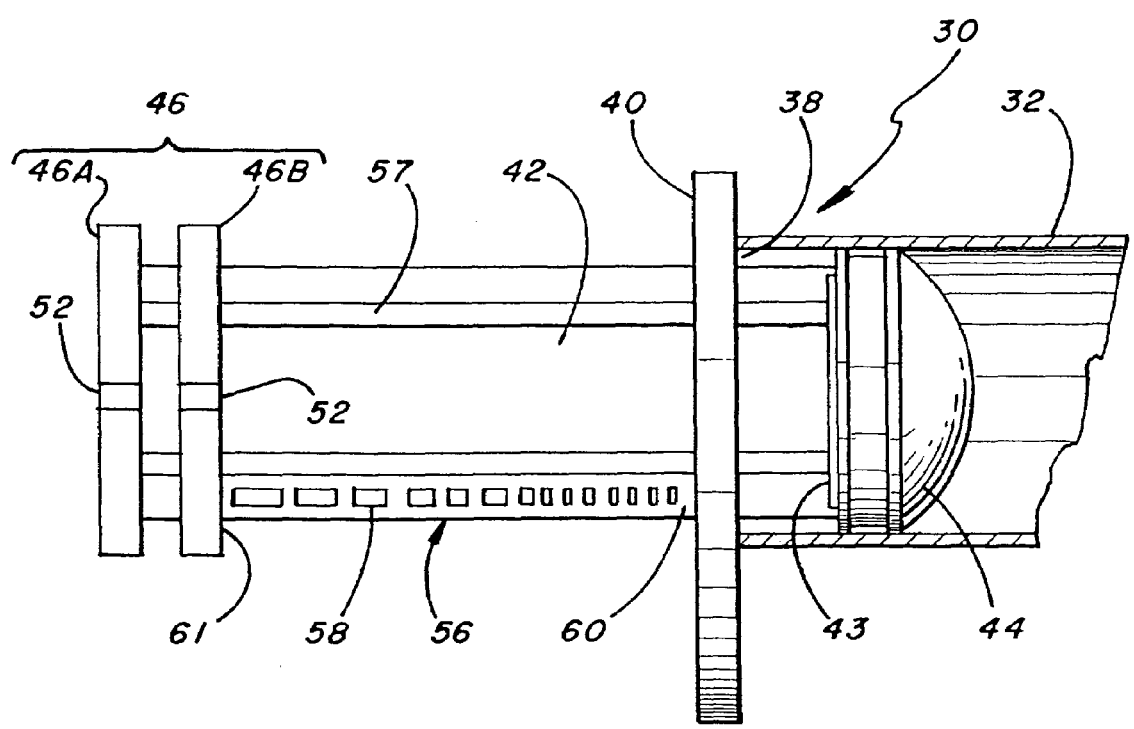
FIG. 6 is a partial cross-section top view of the syringe shown in FIG. 5 showing the markers on the syringe plunger stem usable in indicating near end of infusion and end of infusion, and showing double plunger flanges with guide rail slots formed in both plunger flanges.

An alternate embodiment of a plunger is shown in FIGS. 5 and 6 wherein an "H" section plunger stem 57 is used. It has been found that this configuration provides greater and more even rigidity of the plunger 42. In this embodiment, the syringe body flange 40 includes an opening (not shown) through which the stopper 44 is inserted during assembly of the syringe 30. The opening is marginally smaller than the internal diameter of the syringe barrel and has slots in it corresponding to the stem edges. A disc 43 located just behind the rubber stopper 44 would be just small enough to fit through the hole with the stem edges engaging with the slots. Due to its compliance, the rubber stopper 44 ahead of the disc would compress to fit through the hole in flange 40, then expand to form a seal with the internal wall of the barrel of the syringe. As the disc 46 does not enter the syringe barrel, its size is independent of the syringe barrel diameter.

The slots in the syringe body flange 40 engage the edges of the plunger stem so that the plunger 42 is unable to rotate in relation to the syringe body 32 resulting in greater stability of the syringe and avoiding possible misalignment with markers formed in the plunger, as is discussed below.

The plunger flange 46 has two special features. Referring now in particular to FIGS. 3 and 7, first, two aligned and substantially U-shaped cut-outs 48 are provided in the disks 46A, 46B and each disk 46A, 46B is formed with at least one thread. The embodiment shown in FIGS. 3 and 7 is provided with a half-thread 50 on each disk 46A, 46B. The threaded cut-outs 48 define a threaded portion 50 of the plunger flange 46. The threaded portion 50 effectively comprises a recessed half-nut. In alternate embodiments, threads may also be formed between the disks 46A, 46B such as by making the plunger flange 46 a solid piece without separate disks 46A and 46B. The threads 50 may extend from one end of the flange to the other. The edges of the plunger flange 46 adjacent the threaded portion 50 are formed to guide the threaded portion 50 onto the threaded shaft of the lead screw 54. In this embodiment, they are flared outward from a U-shape to form more of a rounded V-shape. This shape facilitates inserting the syringe onto the threaded shaft making syringe loading faster, easier, and more accurate.

The second feature of the plunger flange 46 is a guide slot 52 formed in the circumferential edges of the disks 46A, 46B at a position opposite the threaded portion 50. Since the plunger flange 46 is circular, the guide slot 52 is diametrically opposite the threaded portion 50. The guide slot is located and shaped to accept a guide rail that keeps the plunger flange against the threaded lead screw shaft. Since the lowermost piece of stem has been omitted from the plunger 42 in one embodiment, and in another embodiment, comprises two parallel stem arms that are spaced apart, the area extending from the threaded portion 50 of the plunger flange 46 to the stopper 44 is clear. This permits placement of the syringe 30 closer to the threaded lead screw shaft 54 resulting in a smaller syringe drive system 64.

Other plunger flange shapes are possible. For example, a plunger flange having a rectangular shape may be used having two guide rail slots formed on the edge opposite the threaded lead screw engaging portion. Two guide rails positioned on either side of the lead screw may add even further stability to the plunger, especially under heavy loads.

Referring now to FIG. 6, one of the stem arms of the plunger 42, in this case the nearmost arm 56, is provided with a linear grid made up of a series of equally spaced markers 58 along the length of the stem arm. The distal markers 58 at the distal end 60, which in this embodiment is the end nearer the stopper 44, are small in comparison to the markers 58 at the proximal end 61, which in this embodiment is the end nearer the plunger flange 46. As explained in detail below, these markers 58 serve in detecting linear motion of the syringe and provide an indication of the amount of fluid remaining in the syringe.

Referring again to FIG. 3, another feature of the syringe 30 is that one edge of the syringe body flange 40 is provided with identification markers 62 which take the form, in this embodiment, of slots. As explained below, these identification markers may be used to provide an indication of the type, e. g., size, of syringe being used. Other types of markers may be used as well as different numbers of them. For example, in one embodiment, it was found to be more effective to use a set of three slots for identification of the syringe.

Turning now to the structure of the syringe driver 66, as shown in FIG. 2, the syringe 30 fits onto selected parts of the syringe driver 66. The syringe driver 66 has a casing 68 upon which a threaded lead screw shaft 54 is rotatably mounted. Preferably, the thread on the shaft 54 is square cut. The shaft 54 is journalled at either end on bearings and is driven by means of a motor (not shown) mounted alongside but spaced apart from the threaded shaft 54. The motor and threaded shaft 54 are connected by a series of gears, including a drive gear 70. The motor may be powered by batteries (not shown) located in the casing 68 or, in the case of a non-ambulatory syringe driver, by main outlet power.

The syringe body 32 rests on the casing 68 and the flange 46 end of the plunger 42 lies parallel with, but spaced apart from, the threaded shaft 54 with the threaded portion 50 directly engaging the threaded shaft 54 such that the threaded portion is engaged with and can follow the threaded shaft. A substantial advantage of the syringe driver system 64 embodying the present invention is that, because no stem arm is present in the plunger flange 42 in the area extending from the threaded portion 50 of the plunger flange 46 to the stopper 44, the threaded shaft 54 can be accommodated in that area so as to take up much less space and effectively be within the confines of the size of the syringe when fully extended. This is shown in FIG. 2 although in this figure, the syringe is not fully extended. This is in stark contrast to the arrangement shown in FIG. 1 for the conventional syringe driver where the threaded shaft is located outside the confines of the syringe.

The casing 68 includes an elongate guide rail 72 which extends parallel to the threaded shaft 54. The guide rail 72 engages the guide slot 52 formed in the plunger flange 46 (FIG. 3). Thus, the plunger flange 46 is securely sandwiched between the guide rail 72 and the threaded shaft 54 and the threaded portion 50 of the plunger flange 46 is securely seated on the threaded shaft 54 such that any rotation of the threaded shaft 54 causes the plunger flange 46 to follow the rotation and drive the plunger 42 into or out of the syringe body 32 as desired. Additionally, use of the guide system prevents the syringe plunger from rotating. The use of a guide rail is particularly advantageous when viscous fluids are in the syringe or a high impedance is encountered downstream which oppose movement of the plunger into the syringe body. Such opposition forces can cause the syringe plunger flange to tend to raise up and off the lead screw thus disengaging. Absent the guide rail holding the plunger flange in contact with the lead screw, infusion of the contents of the syringe may not occur.

The guide rail 72 provides a guide for the travel of the plunger flange 46 and also prevents the threaded portion 50 from being lifted up and away from the threaded shaft 54 during rotation of the shaft 54. Most importantly, because of the direct mechanical engagement between the threaded shaft 54 and the plunger flange 46, there are no moving parts involved between the threaded shaft 54 and the plunger 42 so that there is direct transfer of motion from the shaft 54 to the plunger 42. This arrangement provides a simple and accurate drive system for the syringe driver.

A considerable advantage of this syringe driver arrangement described above and shown in the figures is that, as the majority of syringes are disposable syringes, any syringe used in the syringe driver system embodying the present invention is not going to be subject to wear due to prolonged use since the threaded portion of the plunger is only engaged with the threaded shaft for one use. Thus, each time the syringe driver 66 is loaded with a new syringe 30, a new threaded shaft engaging portion 50 is provided to give an accurate direct mechanical engagement between the plunger 42 and the threaded shaft 54.

The direct engagement of the threaded portion 50 of the plunger flange 46 with the threaded shaft 54 has been tested and the results are exceptionally good. Volumetric tests yielded "trumpet" curves with an accuracy better than 5% at 2 minute intervals at a rate of 5 milliliters per hour.

With continuing reference to FIG. 2, the casing 68 is provided with two opto-electronic detectors in this embodiment. The first detector 74 is used to provide detection of linear movement of the syringe plunger and a warning when the near-end-of-infusion (NEOI) point is being reached, i.e., when the syringe is almost empty and needs replacement. The detector 74 is mounted on the casing 68 adjacent the stem arm 56 upon which the markers 58, 60 (FIG. 6) are formed. The detector 74 is of substantially horse-shoe shape, one end of the horse shoe housing a light source and the other end of the horse shoe housing a pair of detectors located alongside one another such that light from the light source is blocked by the arm 56 so that neither of the detectors are illuminated but, when a marker 58 is positioned between the light source and the detectors, one of the detectors is illuminated. As the syringe plunger travels along the shaft 54, equally spaced dark and light signals are detected by the optoelectronics switch 74. The timing of these signals can be used by a control system to confirm that the plunger is moving at the correct rate. Similarly, a lack of detection of dark and light signals indicates to the syringe driver that no movement of the syringe plunger is occurring. This may be the result of an exhausted syringe, which means that the end of infusion ("EOI") has been reached, thus also providing detection of such condition. The processor of the syringe driver may be programmed to determine the EOI after first detecting the NEOI and to provide an audible and/or visual alarm or other indication of the EOI.

Since the markers at the NEOI point, which is at the proximal end 61, are larger than the markers 58 along the rest of the length of the arm, the larger markers allow the light source of the NEOI detector to illuminate both detectors. This serves as an indication to a control system of the syringe driver that there has been a transition from the smaller markers at the distal end 60 to the larger markers at the proximal end 61 which means that the NEOI point is being approached and the syringe needs to be replaced. Such detection can trigger an alarm, provide a warning light or other form of indication. Clearly, the respective sizes of the markings can be reversed or the shapes or configurations can be changed to obtain the same effect and/or the transition or approach of the NEOI point can be encoded differently on the arm.

The second detector 76 is a syringe identification detector which again comprises a horse-shoe shaped optoelectronic detector having a light source in one of its ends and at least a pair of detectors in its other end. A plurality of such optoelectronic detectors arranged adjacent one another can be provided instead of just one. When a syringe 30 is inserted in the casing 68, the identification markers 62 (FIG. 3) are located between the respective ends of the optoelectronic detector 76, or detectors, so as to provide an indication of the type of syringe inserted in the casing 68 and any other characteristics that the control system of the syringe driver 66 may need to operate in accordance with the specific syringe inserted in the syringe driver. The ability of the syringe driver to automatically recognize a characteristic or characteristics of the syringe, for example the volume of a syringe inserted in the driver, means that this information need not be entered manually thus lessening the possibility of human error.

Referring now to FIG. 8, a simplified drawing of a casing 68 is shown. The casing 68 comprises a generally elongate and rectangular housing comprising a base 80 and a cover 82 that is hinged to the base 80. The casing 68 is dimensioned to accommodate a fully extended syringe 30, although the syringe shown in FIG. 8 is only partially extended in accordance with this particular infusion. Inner details of the case, such as the motor, gears, and lead screw, are not shown for purposes of clarity of illustration of the casing. The motor is controlled by a control panel 84 on the cover 82 and the settings and operation of the driver can be monitored by a display 86 for indicating pump operating parameters such as the infusion rate. The display 86 is located on the cover 82 adjacent the control panel. A control system (not shown) comprising a control circuit or microprocessor is housed within the casing 68 and connected to the control panel and display.

The detectors 74, 76 are linked to the control system to provide information about the type of syringe inserted in the casing 68 as well as the progress of the infusion and proximity of the NEOI point. The control system can be programmed by the control panel 84 to infuse a particular volume of fluid per unit time or to vary the number of infusions of a particular dose required at respective times in accordance with the drug characteristics and any relevant patient information.

The use of the identification markers 62 and the detector 76, or detectors, enables the syringe driver embodying the present invention to recognize the volume of the syringe installed. Based on this information, the control system can be calibrated in milliliters per hour rather than millimeters per hour. This is an improvement over conventional ambulatory syringe drivers which calibrate only in millimeters per hour. Thus, medical staff will find syringe drivers embodying the present invention easier to use since medical staff are well-used to dealing in volumes per unit time rather than lengths per unit time.

Two particular embodiments of a casing 68 are now discussed. The first embodiment is shown in FIGS. 9 and 10. The cover 88 is hinged to the base 90 along the central axis of the threaded shaft 54. A spring plate 92 extends along the base 90 and is provided with a guide rail 72. When the cover 88 is opened, the syringe 30 can be inserted in the cover in a cassette-like manner and the threaded portion 50 of the plunger flange 46 engaged with the threaded shaft 54. The plunger body 32 rests on another area of the base 90 of the casing. The cover 88 can then be closed as shown in FIG. 10. As the cover 88 is pressed down, the spring plate 92 is pushed away from the threaded shaft 54 until the cover is fully closed at which point the guide rail 72 on the spring plate 92 is sprung into position into the guide slot 52 in the plunger flange 46. When the syringe is correctly inserted the spring plate 92 is locked in place by the complete closure of the cover 88. In an alternate embodiment (not shown) the spring plate 92 extends upward and the cover 88 includes a channel. Upon closure of the cover 88 the top of the spring plate 92 engages the channel. In either embodiment, if the syringe 30 is inserted incorrectly the cover 88 cannot be closed.

The internal surface contours of the base 90 correspond closely to the shape of the outer periphery of the syringe body flange 40 thus securing the syringe body 32 within the casing 68 and preventing any turning or re-alignment of the syringe body with respect to the casing. Preferably, a pair of guide ribs (not shown) are molded into the cover 88 to receive a longitudinal edge of the syringe body flange 40 and prevent movement of the syringe body 32 longitudinally with respect to the casing 68.

Referring to FIGS. 11 and 12, in another embodiment of the casing 68, the cover 94 is not hinged about the threaded shaft 54. In this configuration, the guide rail 72 is provided on the lid of the cover 94. The syringe 30 is inserted in the cover 94 and there is enough play when inserting the syringe 30 in the cover 94 for the edge of the plunger flange 46 to slide over the guide rail 72 until the guide rail 72 is engaged in the guide slot 52. Thus, the threaded portion 50 is downwardly depending and pointing substantially towards the threaded shaft 54. The cover 94 is hinged on the far side of the casing 68 to bring the threaded portion 50 into direct engagement with the threaded shaft 54 at which point the cover 94 is closed on the base portion 96 as shown in FIG. 12. Thus, the action of loading and closing the casing 68, in both the embodiments shown in FIGS. 9 to 12, locates the threaded portion 50 of the plunger flange 46 into direct engagement with the threaded shaft 54. The successful closing of the casing 68 is preferably monitored by an optical switch, microswitch or the like which disables the motor and/or any control devices so as to prevent the syringe driver from working without a syringe being properly loaded.

In one embodiment, conveniently, different volumes of syringes all have common exterior characteristics allowing all volumes of syringes to be correctly loaded in the same syringe driver. The volume of the syringe can then be determined by using the coded identification markers 62 which are molded into the syringe body flange 40 of the syringe body 32.

Although the syringe disclosed in the above embodiments has been provided with additional features, the syringe can still function as a normal syringe for use without the syringe driver. Conveniently, the syringes for use with the syringe driver are sold as dedicated units for loading in the syringe driver and may come in the form of pre-filled syringes. Preferably, the syringes 30 used with the syringe driver embodying the present invention have a higher width to length ratio than normal syringes so that the length of the syringe is minimized for a given volume of syringe. It is envisaged that the use of non-cylindrical syringe bodies could be advantageous as a means of registering the syringe body 32 in the casing 68 or to provide a more convenient case shape to the user.

While the above-mentioned examples describe a syringe driver for a single syringe, a syringe driver using the same concepts can be provided for driving multiple syringes. The above-mentioned examples of the plunger involve the use of a threaded portion 50 on the plunger flange 46 for engaging the threaded lead screw shaft 54. The invention, however, can still be implemented by engaging an unmodified edge of a plunger flange 46 directly with the threaded shaft 54, the edge of the plunger flange sitting between the threads of the threaded shaft 54. It is envisaged that the arrangement of the guide slot 52 and guide rail 72 can be reversed or otherwise implemented. For example, the guide rail 72 can be replaced with an elongate channel running substantially parallel to the threaded shaft 54 and the guide slot 52 replaced by a projection extending from the plunger for reception in the channel. Alternatively, an elongate plunger stem arm may be formed on the plunger at a position substantially opposite the position at which the plunger is engaged with the threaded shaft and a guiding system comprising the arm and a bifurcated element are located on the casing 68 to straddle the arm.

The syringe driver can also be provided with means to sense that a syringe has been removed from the casing or the casing is empty. Such sensing means can comprise an optical detector, microswitch or the like. The sensing means can provide a signal to a stop valve or the like to close the fluid line to a patient to prevent syphoning of the medicament in the line when the syringe has been removed from the casing or if the casing is empty.

Figure 13:
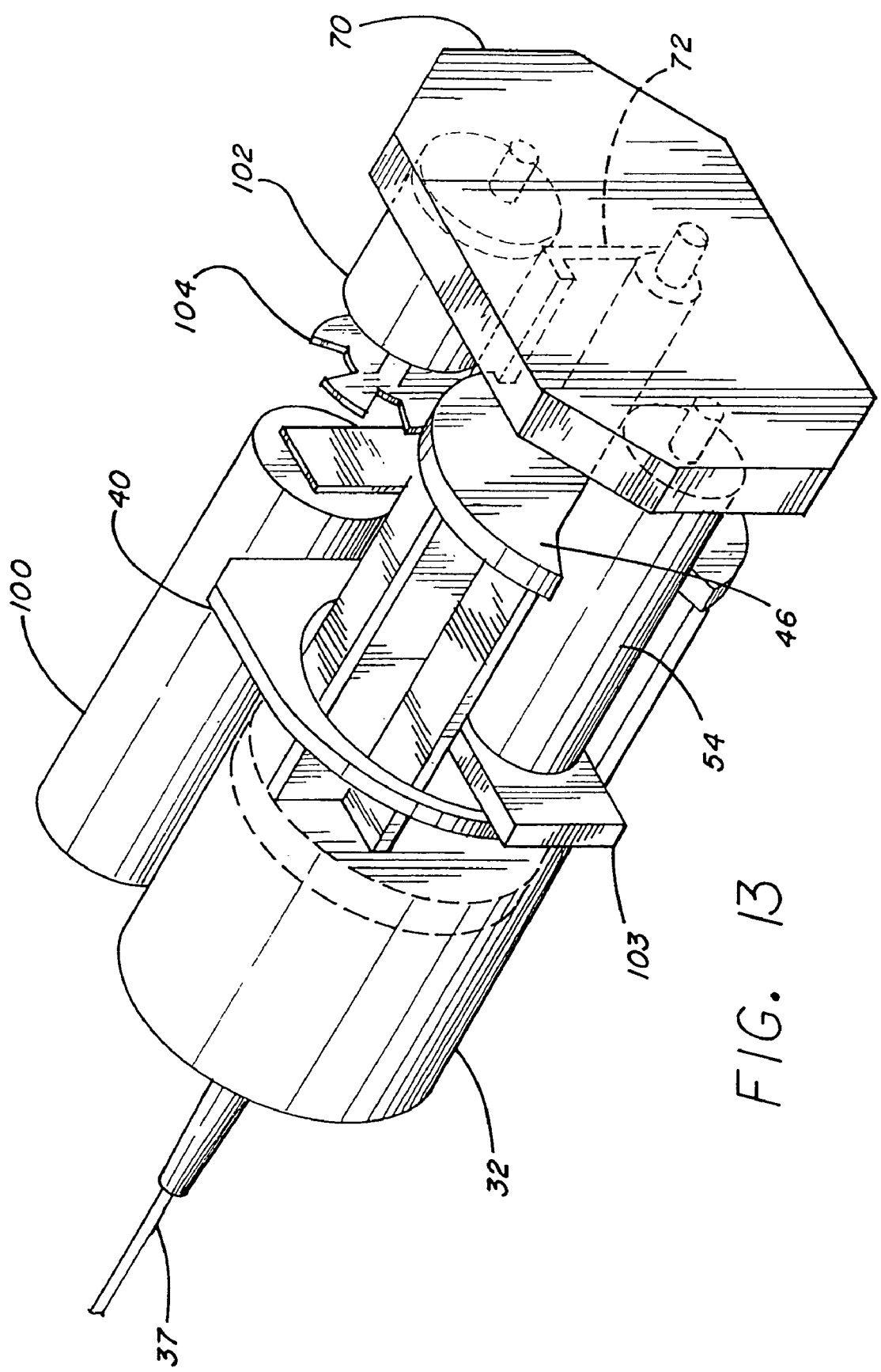
FIG. 13 presents a block diagram of a layout of a syringe drive system in accordance with aspects of the invention.

Referring now to FIG. 13, a schematic, block diagram of an example of a compact syringe drive system incorporating aspects of the invention is presented. Additionally, the compact syringe drive system of FIG. 13 includes aspects of FIGS. 9 and 10. In this layout, the syringe body 32 is located adjacent the battery 100. At the opposite end, the motor 102 is connected to a gear drive 70 which drives the lead screw 54. The internal components of the gear drive 70 are not shown in the interest of retaining clarity in the drawing. A motor encoder disk 104 for use in detecting the speed and direction of the motor is provided. An optical switch (not shown) is mounted so as to read the encoder disk 104. A partial view of a bearing block 103 supporting one end of the lead screw 54 is shown. This arrangement results in a compact syringe drive system.

Although the system for detecting the near-end-of-infusion was shown and described above as a series of markers formed into a stem arm, other approaches may be possible. One approach that may be used is that shown in U.S. Pat. No. 5,236,416 to McDaniel et al. where a stationary detector is used in conjunction with a marker. The marker moves with the syringe plunger and interacts with the stationary detector, which may take the form, of a potentiometer. In the present case, a marker, such as spur, could be molded or otherwise formed onto the plunger flange 46 or other movable part associated with the plunger. A potentiometer functioning as the detector could be located in the pump case in a position such that the spur of the plunger flange 46 would contact the potentiometer during its entire range of travel. The output of the potentiometer could then be used to monitor the position of the plunger flange 46 and thus the plunger so that the near-end-of-infusion point could be determined.

Thus the syringe driver of the present invention has fewer parts in that a driver block is not used with the resulting decrease in expense and increase in manufacturing ease. Additionally, the system is more compact and the need for maintenance should be lowered because of this lack of a driver block which is prone to wear.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A syringe for use in a fluid delivery apparatus having a threaded shaft, said syringe comprising:
   a syringe body;
   a plunger stem having a distal end and a proximal end;
   a stopper positioned at the distal end of the stem, the stopper sized to fit within the syringe body; and
   a flange positioned at the proximal end of the stem and outside of the syringe body, the flange extending radially outwardly from the stem and having a threaded portion sized to engage the threaded shaft, wherein the flange has radially outwardly facing edges, the threaded portion being adjacent the edges, the edges formed to guide the threaded portion onto the threaded shaft; wherein the plunger stem comprises an open area in the area extending from the threaded portion to the stopper to receive the threaded shaft.

2. The syringe of claim 1 wherein the threaded portion is molded into the flange.

3. The syringe of claim 1 wherein a guide slot is provided on the plunger substantially opposite the threaded portion, the guide slot configured to receive a guide rail to securely seat the threaded portion on the threaded shaft.

4. The syringe of claim 1 wherein the plunger stem comprises a plurality of markers adapted to indicate the movement and position of the plunger within the syringe body.

5. The syringe of claim 4 wherein the plurality of markers comprise a linear grid.

6. The syringe of claim 4 wherein an area of the plunger between the markers is substantially opaque and the markers comprise substantially transparent portions.

7. The syringe of claim 1 wherein the plunger includes a marker indicative of the position of the plunger, the marker mounted so as to move with the plunger.

8. The syringe of claim 1 wherein the syringe body includes a syringe identification marker indicative of a characteristic of the syringe; and
   the system further comprising a syringe detection system including a detector for detecting the identification marking of the syringe, the syringe detector system adapted to provide a signal in accordance with the identification marking detected.

9. The syringe of claim 1 wherein the flange includes a cut-out within which the threaded portion is disposed and the edges of the flange flare away from the cut-out to give the cut-out a non-clamping rounded V-shape wherein the V-shape guides the flange over the threaded shaft to engage the threaded portion with the threaded shaft but does not exert a clamping force to the threaded shaft.

10. A syringe for use in a fluid delivery apparatus having a threaded shaft, said syringe comprising:
    a syringe body;
    a plunger stem having a distal end and a proximal end;
    a stopper positioned at the distal end of the stem, the stopper sized to fit within the syringe body; and
    a flange positioned at the proximal end of the stem and outside of the syringe body, the flange extending radially outwardly from the stem, the flange having a thread facing outwardly, the thread sized to engage the threaded shaft, wherein the flange includes a cut-out within which the thread is disposed, the flange having edges that flare away from the cut-out to give the cut-out a non-clamping rounded V-shape wherein the V-shape guides the flange over the threaded shaft to engage the thread with the threaded shaft but does not exert a clamping force to the threaded shaft;
    wherein a guide slot is provided on the plunger substantially opposite the thread, the guide slot configured to receive a guide rail to securely seat the thread on the threaded shaft.

11. The syringe of claim 10 wherein the thread is molded into the flange.

12. The syringe of claim 10 wherein the plunger stem comprises an open area in the area extending from the thread to the stopper to receive the threaded shaft.

13. The syringe of claim 10 wherein the plunger comprises a plurality of markers adapted to indicate the movement and position of the plunger within the syringe body.

14. The syringe of claim 13 wherein the plurality of markers comprise a linear grid.

15. The syringe of claim 13 wherein an area of the plunger between the markers is substantially opaque and the markers comprise substantially transparent portions.

16. The syringe of claim 10 wherein the plunger includes a marker indicative of the position of the plunger, the marker mounted so as to move with the plunger.

17. The syringe of claim 10 wherein the syringe includes a syringe identification marker indicative of a characteristic of the syringe.

18. A syringe for use in a fluid delivery apparatus having a threaded shaft, said syringe comprising:
   a syringe body;
   a plunger stem having a distal end and a proximal end;
   a stopper positioned at the distal end of the stem, the stopper sized to fit within the syringe body; and
   a flange positioned at the proximal end of the stem and outside of the syringe body, the flange comprising radially outwardly facing edges and a threaded portion adjacent the edges, the threaded portion sized to engage the threaded shaft, wherein the flange includes a cut-out within which the threaded portion is disposed and edges of the flange flare away from the cut-out to give the cut-out a non-clamping rounded V-shape wherein the V-shape guides the flange over the threaded shaft to engage the threaded portion with the threaded shaft but does not exert a clamping force to the threaded shaft;
   wherein the plunger stem comprises an open area in the area extending from the threaded portion to the stopper to receive the threaded shaft.

19. The syringe of claim 18 wherein the threaded portion is molded into the flange.

20. The syringe of claim 18 wherein a guide slot is provided on the plunger substantially opposite the threaded portion, the guide slot configured to receive a guide rail to securely seat the threaded portion of the flange on the threaded shaft.

21. The syringe of claim 18 wherein the plunger comprises a plurality of markers adapted to indicate the movement and position of the plunger within the syringe body.

22. The syringe of claim 21 wherein the plurality of markers comprise a linear grid.

23. The syringe of claim 21 wherein an area of the plunger between the markers is substantially opaque and the markers comprise substantially transparent portions.

24. The syringe of claim 18 wherein the plunger includes a marker indicative of the position of the plunger, the marker mounted so as to move with the plunger.

25. The syringe of claim 18 wherein the syringe includes a syringe identification marker indicative of a characteristic of the syringe.

* * * * *